(12) United States Patent
Hartkopf-Ceylan (10) Patent No.: US 11,490,962 B2
(45) Date of Patent: Nov. 8, 2022

(54) HAND PIECE FOR HANDLING A OPTICAL FIBER DURING A LASER-SURGICAL INTERVENTION

(71) Applicant: LISA Laser Products GmbH, Katlenburg-Lindau (DE)

(72) Inventor: Kay-Siebo Hartkopf-Ceylan, Northeim (DE)

(73) Assignee: LISA LASER PRODUCTS GMBH, Katlenburg-Lindau (DE)

( * ) Notice: Subject to any disclaimer, the term of this patent is extended or adjusted under 35 U.S.C. 154(b) by 209 days.

(21) Appl. No.: 16/691,651

(22) Filed: Nov. 22, 2019

(65) Prior Publication Data

US 2020/0163717 A1 May 28, 2020

(30) Foreign Application Priority Data

Nov. 22, 2018 (DE) .................... 20 2018 106 650.1

(51) Int. Cl.
*A61B 18/24* (2006.01)
*G02B 6/36* (2006.01)
*A61B 17/00* (2006.01)
*A61B 18/00* (2006.01)
*A61B 18/20* (2006.01)

(52) U.S. Cl.
CPC ............ *A61B 18/24* (2013.01); *G02B 6/3616* (2013.01); *A61B 2017/00469* (2013.01); *A61B 2018/00023* (2013.01); *A61B 2018/2005* (2013.01)

(58) Field of Classification Search
CPC ............... A61B 18/24; A61B 18/22; A61B 2017/00469; A61B 2017/00464; A61B 2017/0046; A61B 2018/00005; A61B 2018/00011; A61B 2018/00017; A61B 2018/00023; A61B 2018/00029; A61B 2018/00035; A61B 18/20; A61B 2018/2005; A61B 18/201; G02B 6/3616; G02B 6/362; G02B 6/3624
USPC .......................................................... 606/16
See application file for complete search history.

(56) References Cited

U.S. PATENT DOCUMENTS

6,165,198 A * 12/2000 McGurk .......... A61B 17/12022
606/200
8,262,671 B2 * 9/2012 Osypka ............. A61M 25/0668
606/108
2003/0199860 A1 10/2003 Loeb et al.
2009/0093800 A1 4/2009 Auld et al.
(Continued)

*Primary Examiner* — Aaron F Roane
(74) *Attorney, Agent, or Firm* — Thomas | Horstemeyer, LLP (57) ABSTRACT

A hand piece for handling an optical fiber during a laser-surgical intervention comprises a handle body elongated along a main axis and having a through hole extending along the main axis. A guide tube having a tube lumen aligned and communicating with the through hole is attached to the handle body. A fixing device is provided in the handle body for fixing the optical fiber extending through the through hole and the tube lumen in direction of the main axis. The guide tube is made of a shaped memory alloy, which has a transition temperature between 50° C. and 120° C., and which has a straight base shape. Below the transition temperature, the guide tube is bendable by plastic deformation out of the straight base shape into a curved shape, and, when heated up above the transition temperature, the guide tube returns to its straight base shape.

20 Claims, 4 Drawing Sheets

(56) References Cited

U.S. PATENT DOCUMENTS

| | | | | |
|---|---|---|---|---|
| 2009/0248004 A1* | 10/2009 | Altshuler | ............... | A61B 18/18 |
| | | | | 606/33 |
| 2011/0065997 A1* | 3/2011 | Hamer | ............. | A61B 17/32002 |
| | | | | 600/159 |
| 2012/0303010 A1* | 11/2012 | Vijfvinkel | ........... | A61F 9/00781 |
| | | | | 606/6 |
| 2014/0005642 A1 | 1/2014 | Scheller et al. | | |
| 2016/0262932 A1* | 9/2016 | Mansour | ............. | A61F 9/00821 |

\* cited by examiner

HAND PIECE FOR HANDLING A OPTICAL FIBER DURING A LASER-SURGICAL INTERVENTION

CROSS REFERENCE TO RELATED APPLICATIONS

This application claims priority to German utility model application No. 20 2018 106 650.1 entitled "Handstück zur Handhabung einer Lichtleiterfaser bei einem laserchirurgischen Eingriff" and filed on Nov. 22, 2018.

FIELD OF THE INVENTION

The present invention relates to a hand piece for handling an optical fiber during a laser-surgical intervention. More particular, the present invention relates to hand piece comprising a handle body elongated along a main axis and a guide tube attached to one end of the main body, wherein a tube lumen of the guide tube is aligned and communicates with a through hole running through the handle body along the main axis; and a fixing device for the optical fiber extending through the through hole and the tube lumen of the guide tube, the fixing device being arranged in the area of the through hole within the handle body.

Such a hand piece may, for example be used for handling an optical fiber, by which laser light is guided from a laser to the location of a surgical intervention to heat up water containing tissue or other objects. This heating up may serve for obliterate tissue, cutting tissue, evaporating tissue, shattering objects and the like. The laser light guided by the optical fiber may, for example, have a wavelength in a range of 2 µm at which water has a particularly high absorption.

BACKGROUND OF THE INVENTION

Hand pieces for handling optical fibers are subject to various requirements. These requirements include an easy sterilization of the entire Hand piece, a reversible fixation of the optical fiber along its lengths within the hand piece, a usability of the hand piece in MRT-imaging of the location of the surgical intervention, and so on. The reversible fixation is needed for feeding forward and cut the optical fiber when its present tip has been used up, and for adapting the optical fiber to different spatial positions of the location of the surgical intervention.

For catheters, it is known to use guiding wires made of nitinol, which are arranged within the catheter lumen for putting the catheter in place. Here, the special elastic properties, particularly the super-elasticity, in the area of and above its transition temperature are utilized.

US patent application publication US 2016/262932 A1 discloses the use of a guide tube made of super-elastic nitinol in a hand piece for handling an optical fiber during a laser-surgical intervention. The hand piece includes a device for elastically bending the tip of the super-elastic guide tube in a curved shape.

With stents made of nitinol, the properties of nitinol as a shape memory alloy are utilized. The stents are implanted while being in a radially compressed state, and they expand up to their original diameter when they exceed the transition temperature of the nitinol at the implantation site. For this purpose, the transition temperature of the nitinol is tuned to be below the body temperature of the patient.

Active endoscopes are known whose shape can be voluntarily changed by means of elements made of shape memory alloys.

There still is a need of a hand piece for handling an optical fiber during a laser-surgical intervention, which, despite a high functionality, can be sterilized easily and securely to enable its repeated use.

SUMMARY OF THE INVENTION

The present invention relates to a hand piece for handling an optical fiber during a laser-surgical intervention. The hand piece comprises a handle body elongated along a main axis. The handle body has a through hole extending along the main axis. Further, the hand piece comprises a guide tube attached to the handle body. The guide tube has a tube lumen aligned and communicating with the through hole. The hand piece also comprises a fixing device configured for, in direction of the main axis, fixing the optical fiber extending through the through hole and the tube lumen of the guide tube. The fixing device is located in an area of the through hole in the handle body. The guide tube is made of a shaped memory alloy which has a transition temperature between 50° C. and 120° C. The guide tube has a straight base shape. Below the transition temperature, the guide tube is bendable by plastic deformation out of the straight base shape into a curved shape; and, when heated up above the transition temperature, the guide tube returns to its straight base shape Further, the present invention relates to an optical fiber handling apparatus comprising a first handle part and a second handle part screwed together by rotation about a main axis and together forming a handle elongated along the main axis. The handle has a through hole extending along the main axis through the first handle part and the second handle part. The optical fiber handling apparatus further comprises a guide tube made of a shaped memory alloy, which has a transition temperature in a range from 60 and 90° C., and attached to the first handle part. The guide tube has a tube lumen aligned and communicating with the through hole such as to provide a continuous passage for an optical fiber through the handle and the guide tube. The guide tube has a straight base shape extending along the main axis. Below the transition temperature, the guide tube is bendable by plastic deformation out of the straight base shape into a curved shape, and the guide tube, after a plastic deformation taking place below the transition temperature, returns to the straight base shape upon exceeding the transition temperature.

Further, the optical fiber handling apparatus comprises a ring-shaped elastic seal arranged between the first handle part and the second handle part. The ring shaped seal is compressed by screwing the first handle part and the second handle part together so that it is pressed against the optical fiber extending through the through hole such as to seal the through hole around the optical fiber and such as to fix the optical fiber with regard to the handle in direction of the main axis. The optical fiber handling apparatus also comprises a cooling fluid supply connector arranged at the first handle part and communicating with the through hole up to the elastic seal, and, via the through hole, with the tube lumen of the guide tube Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components of the drawings are

DETAILED DESCRIPTION

The hand piece according to the invention for handling an optical fiber during a laser-surgical intervention comprises a handle body elongated along a main axis and a guide tube attached to one end of the handle body. A tube lumen of the guide tube is aligned and communicates with a through hole running through the handle body along the main axis. The hand piece further comprises a fixing device for the optical fiber extending through the through hole and the tube lumen of the guide tube. The fixing device is located in the area of the through hole within the handle body. The guide tube is made of a shaped memory alloy, which has a transition temperature between 50° C. and 120° C., wherein the guide tube has a straight base shape to which it returns after a plastic deformation taking place below the transition temperature upon exceeding the transition temperature.

At room temperature and at the body temperature of a human being, the guide tube of the hand piece according to the invention is significantly below the transition temperature of the shaped memory alloy of which the guide tube is made. Thus, in the temperature range of its use during a laser-surgical intervention, the guide tube is dimensionally stable, and is has a comparatively high stiffness. Particularly it is not super-elastic. However, the guide tube can be plastically cold formed to provide it with a desired spatial course or curved shape. At a typical small outer diameter of the guide tube of a view millimeters and a typical wall thickness of the guide tube of a view tenth of millimeters, no high forces are required for the plastic deformation of the guide tube. Thus, the guide tube can be easily bent into a shape into which it is suited for guiding the optical fiber with a desired orientation to the location of the laser-surgical intervention. The shape provided to the guide tube via the plastic deformation is not lost in the regular use of the guide tube. However, it is removed so that the guide tube returns to its straight base shape, when the guide tube is heated up beyond its transition temperature, which is in the range from 50° C. to 120° C. The actual transition temperature of the shaped memory alloy, of which the guide tube is made, is to be adjusted in the hand piece according to the invention such that it is not reached in the regular use of the hand piece. On the other hand, the transition temperature of the shaped memory alloy is preferably selected such that it is exceeded in regular cleaning and sterilization of the hand piece according to the invention. The straight base shape of the guide tube facilitates its cleaning. Further, the straight base shape, to which the guide tube returned, indicates that it has been heated up to a temperature above its transition temperature. This is an indication of its regularly executed cleaning at an increased temperature.

With its straight base shape, the guide tube of the hand piece according to the invention preferably extends along the main axis so that it continues the through hole through the handle body, with which is aligned, in a straight line.

Preferably, the transition temperature of the shaped memory alloy, of which the guide tube of the hand piece according to the invention is made, is within a range from 60 to 90° C. Typically, there is a danger that biological tissue is seriously damaged even due to a comparatively short time contact with an object having a temperature of 60° C. or more. Correspondingly, it is usual that a laser, to which the optical fiber is coupled and which couples the laser light into the optical fiber, is switched off when this temperature is reached at the tip of the optical fiber. Thus, in the regular use of the hand piece according to the invention, no temperature of the guide tube of 60° C. or more occurs. However, a temperature of the guide tube of up to 90° C. is quickly reached in a water bath, which is at a temperature close to the boiling point of water. The transition temperature of the shaped memory alloy may particularly be in a range from 62 to 65° C., which refers to the transition temperature of the shaped memory alloy at the beginning. It is known that this transition temperature of the shaped memory alloy at the beginning tends to increase with repeated pronounced cold deformation of an object made thereof, i. e. of the guide tube.

A cooling fluid supply connector may be attached to the handle body of the hand piece according to the invention. The cooling fluid supply connector may communicate with the tube lumen of the guide tube via the through hole. A cooling fluid hose may be connected to the cooling fluid supply connector to supply cooling fluid, particularly water, which then flows through the guide tube along the optical fiber to the location of the respective surgical intervention. The cooling fluid thus cools the guide tube and the fiber-optical light guide as well as tissue adjoining the location of the surgical intervention.

The handle body of the hand piece according to the invention may have two handle parts, which are screwed together about the main axis. Between the two handle parts, a ring-shaped elastic seal may be arranged which, as a part of the fixing device, abuts against the optical fiber running there through upon screwing the two handle parts together. The seal abutting against the optical fiber holds it with an elastic clamping force, which is increased with the screwing together of the two handle parts. At the same time, the seal seals the through hole around the optical fiber. Further, the elastic seal also results in that the two handle parts are not inadvertently screwed apart, even if they are not screwed against each other to such an extent that they stiffly braced against each other.

If a cooling fluid supply connector is attached to the handle body of the hand piece according to the invention, the sealing of the through hole around the optical fiber achieved with the ring-shaped seal is arranged on that side of the cooling fluid supply connector facing away from the guide tube. Thus, the sealing inhibits that cooling fluid leaks through the through hole at the end of the handle body facing away from the guide tube. Further, with a suitable formation and arrangement, the ring-shaped seal inhibits leaking of the cooling fluid between the two handle parts of the handle body.

The guide tube of the hand piece according to the invention may be inserted in a guide tube socket extending beyond the handle body. Here, the guide tube can be releasably or permanently anchored in the guide tube socket. Both kinds of anchoring can be realized by friction fit, for example. The guide tube socket stabilizes the guide tube at the transition to the handle body and inhibits kinking of the guide tube at this transition.

An elastic aspiration hose may be arranged on the guide tube of the hand piece according to the invention. An inner diameter of the aspiration hose may be larger than an outer diameter of the guide tubes so that an annular space remains between the guide tube and the aspiration hose. Via this annular space, for example, smoke may be aspirated out of an intervention area in front of the front end of the guide tube.

To apply an under pressure to the aspiration hose, which is required for such an aspiration, an aspiration connector communicating with the aspiration hose may be provided, to which an aspiration line can be connected. This aspiration connector may be attached to the handle body or a separate aspiration manifold pushed over the guide tube. Such an aspiration manifold may be permanently connected to the aspiration hose on the guide tube. If the aspiration connector is attached to the handle body, the aspiration hose may be pushed on an aspiration hose fitting, which is arranged around the guide tube in the area of the transition of the guide tube into the handle body.

Particularly, the shaped memory alloy, of which the guide tube of the hand piece according to the invention is made, may be a nickel-titan-alloy which is also designated as nitinol.

Particularly, it can be nitinol SM 495, i. e. a nickel-titan-alloy consisting by 54.5% of nickel, whose transition temperature, depending on a pretreatment, is in a range between 50 to 80° C. Particularly, this transition temperature may be about 63 to 64° C. due to a suitable pretreatment.

All elastic components of the hand piece according to the invention may be made of silicone rubber. Silicone rubber displays a sufficient temperature resistance to endure a thermal sterilization. The parts of the hand piece according to the invention, which may be made of silicone rubber, particularly include the ring-shaped elastic seal between the two handle parts, the aspiration hose and any manifold connected thereto.

The handle body and the handle parts, respectively, of the hand piece according to the invention may be made of polyether ether ketone (PEEK). PEEK is a plastic, which is temperature stable up to over 300° C. The formation of the handle body and the handle parts, respectively, of PEEK also allows for using the hand piece according to the invention within a magnetic resonance tomograph. The magnetism of nitinol is only low, and with an only small wall thickness of the guide tube there is no danger of a pronounced heating up of the guide tube by eddy currents excited by the alternating magnetic field prevalent in an MRT.

For a utilization outside of MRT, a formation of the handle body and the handle parts, respectively, of coated aluminum is preferred, in which the alternating magnetic fields in an MRT would generate eddy currents resulting in a significant increase in temperature. The coating of the aluminum has the purpose of a passivation of the surface of the aluminum. The coating of the aluminum may be applied by anodizing. A coating of the aluminum with diamond-like carbon (DLC), by which a durable surface with a high hardness is achieved, is preferred. Further, DLC is laser-inscribable so that information can be written on the handle body with a laser. The desired surface hardness of the aluminum may additional be achieved in that the surface of the aluminum is glass bead blasted prior to being coated. Glass bead blasting results in a surface hardening by cold working, which is not lost in the aluminum at the temperatures reached in sterilizing the hand piece according to the invention. Generally, the aluminum of the handle body or the handle parts may also be alloy hardened. A pronounced alloy hardening with, for example, copper, however increases the efforts which have to be spent in working the aluminum for forming the handle body or the handle parts, respectively.

When the hand piece according to the invention has a cooling fluid supply connector, it is preferably made of PEEK. Generally, however, it may also be made of stainless or high-grade steel. If present, the guide tube socket of the hand piece according to the invention is preferably made of PEEK or of stainless or high-grade steel, and the aspirator connector of the hand piece according to the invention, if present, is preferably made of PEEK or silicone rubber. The materials mentioned here can be sterilized and they are, at least to the extent of the parts mentioned, usable in an MRT without problem.

Figure 1:
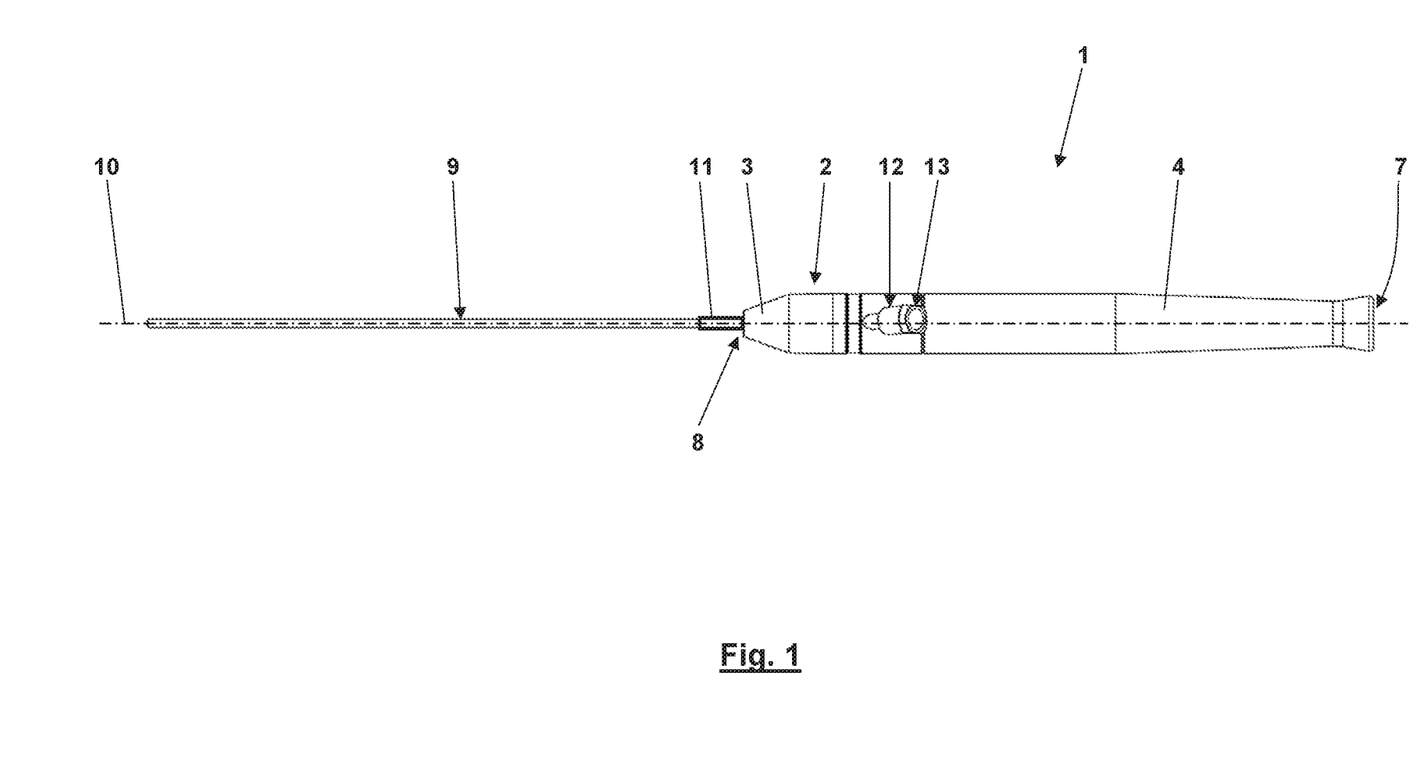
FIG. 1 is a side view of an embodiment of the hand piece according to the invention.
Figure 2:
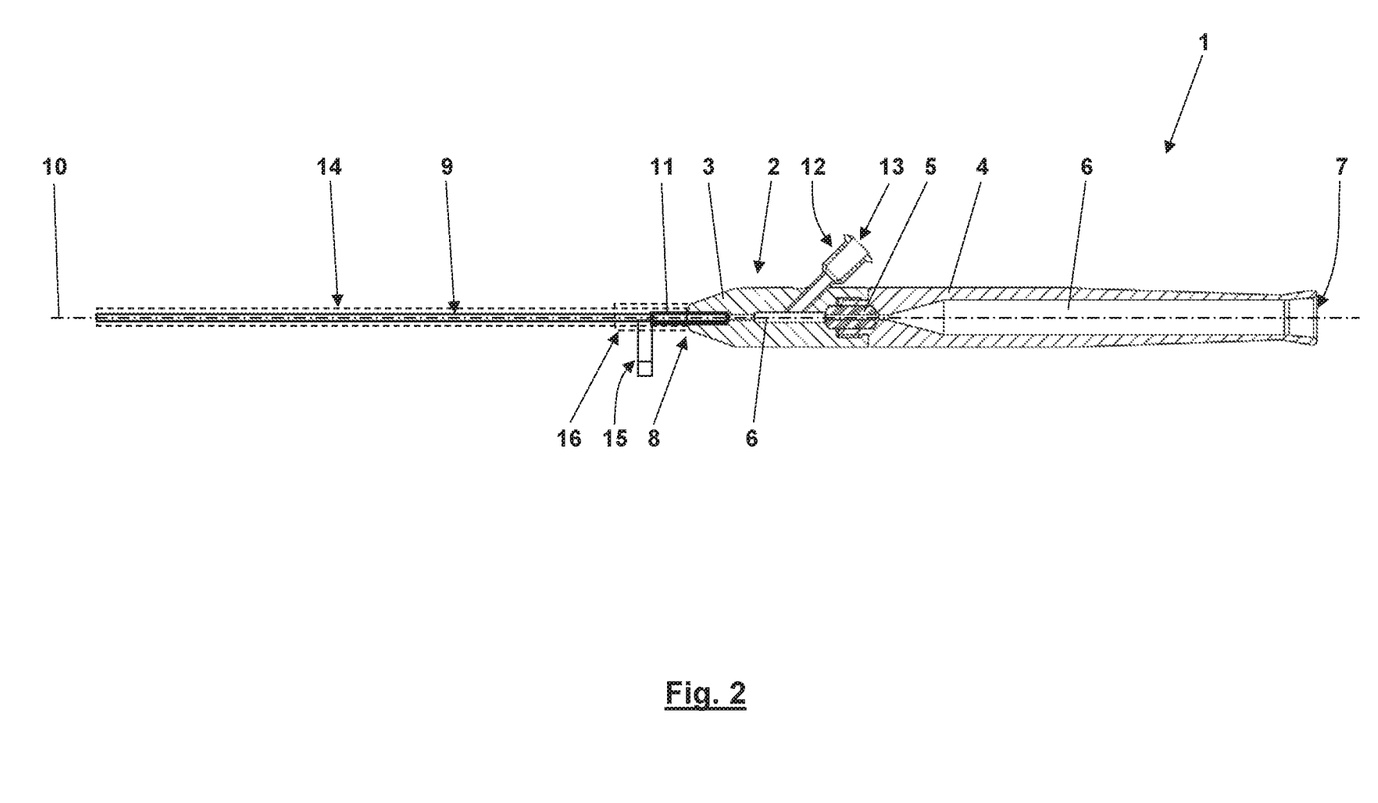
FIG. 2 is a view of a longitudinal section through the hand piece according to FIG. 1 along a section line A-A indicated in FIG. 1.

Now referring in greater detail to the drawings, the hand piece 1 depicted in FIGS. 1 and 2 has a handle body 2 includes two handle parts 3 and 4, which are screwed together. A ring-shaped elastic seal 5 is arranged between the handle parts 3 and 4. When screwing the handle parts 3 and 4 together, the seal 5 is compressed. Thus, with a holding force, the seal 5 abuts against an optical fiber, which is not depicted here and for the handling of which the hand piece 1 is provided. The optical fiber runs through a through hole 6 in the handle body 2. This through hole 6 is divided by the seal 5 between the handle parts 3 and 4 and sealed around the optical fiber. The seal 5 also seals the handle parts 3 and 5 against each other. Towards a back end 7 of the handle body 2, the diameter of the through hole 6 increases, so that the optical fiber here runs through the handle body 2 with radial play and is protected against kinking at the back end 7. At a front end 8 of the handle body 2 facing away from the back end 7, a guide tube 9 for the optical fiber is attached whose tube lumen is aligned and communicates with the through hole 6. The guide tube 9 has a straight base shape in which it runs straight on the main axis 10, along which the handle body 2 is elongated and along which the through hole 6 extends. At the front end 8 of the handle body 2, the guide tube 9, at its transition into the handle body 2, is reinforced by a guide tube socket 11. A cooling fluid connector 12 is attached to the front handle part 2. The cooling fluid connector 12 communicates with the through hole 6 at the front side of the seal 5. A cooling fluid may be injected via the cooling fluid connector 12, which then flows along the optical fiber through the guide tube 9. The cooling fluid supply connector 12 is provided with a standardized syringe connector 13.

A aspirator hose 14 arranged on the guide tube 9 is depicted in FIG. 2 only and schematically only. The inner diameter of the aspirator hose 14 is larger than the outer diameter of the guide tube 6 so that, by aspirating at an aspirator connector 15 attached to the aspirator hose 14, for example, smoke gas can be aspirated out of an area in front of the guide tube 19. The aspirator connector is attached to a manifold 16 to which the aspirator hose 14 is also attached. The aspirator hose 14 is elastic, and it may particularly be made of silicone rubber. Thus, it may participate in shape changes of the guide tube 9. Due to its formation of a shaped memory alloy with a transition temperature of about 65° C., such shape changes of the guide tube 9 are not only possible in the elastic but also in the plastic range.

Figure 3:
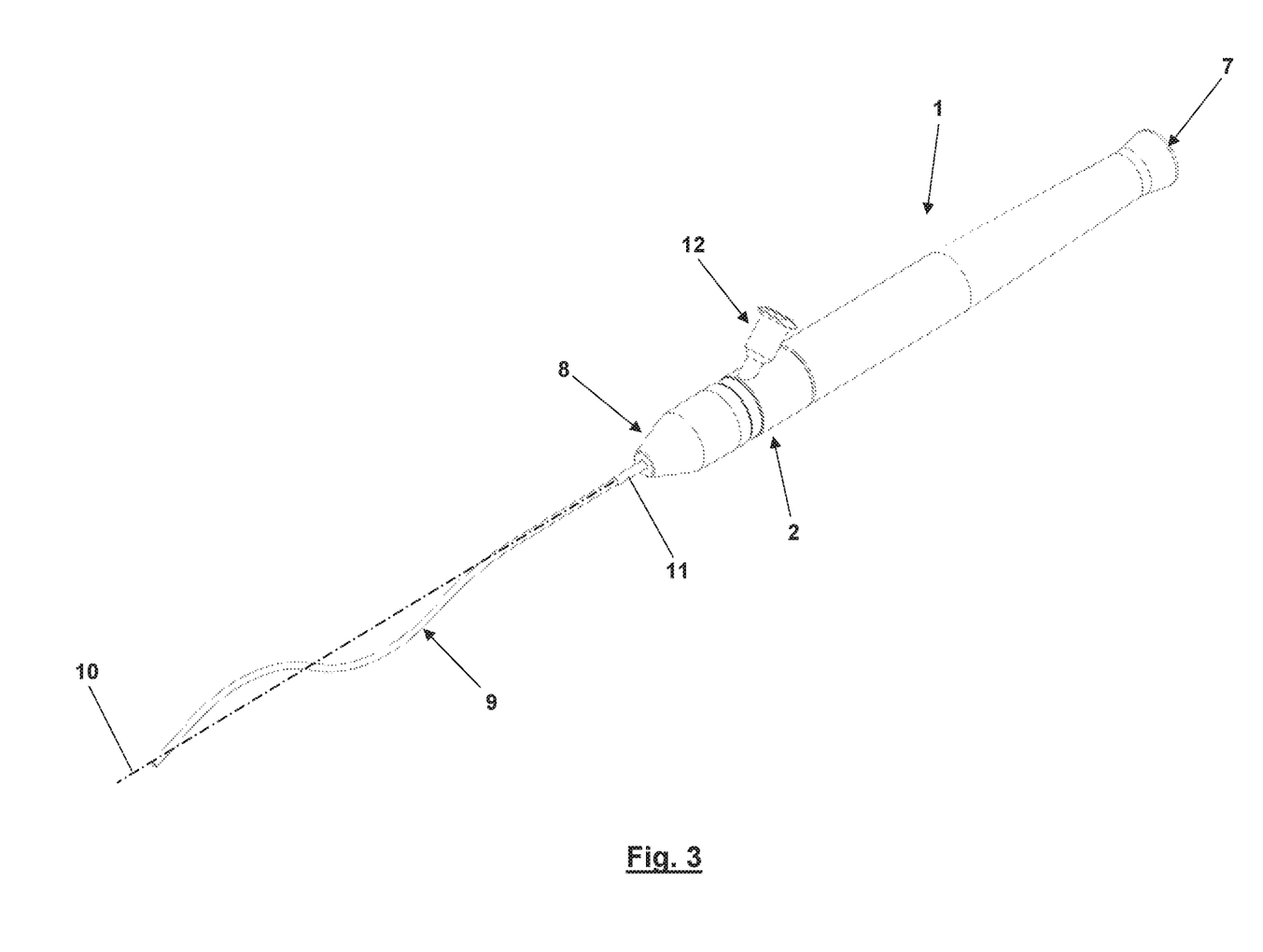
FIG. 3 is a perspective view of the hand piece according to the invention after plastic deformation of its guide tube into a freely bent shape.
Figure 4:
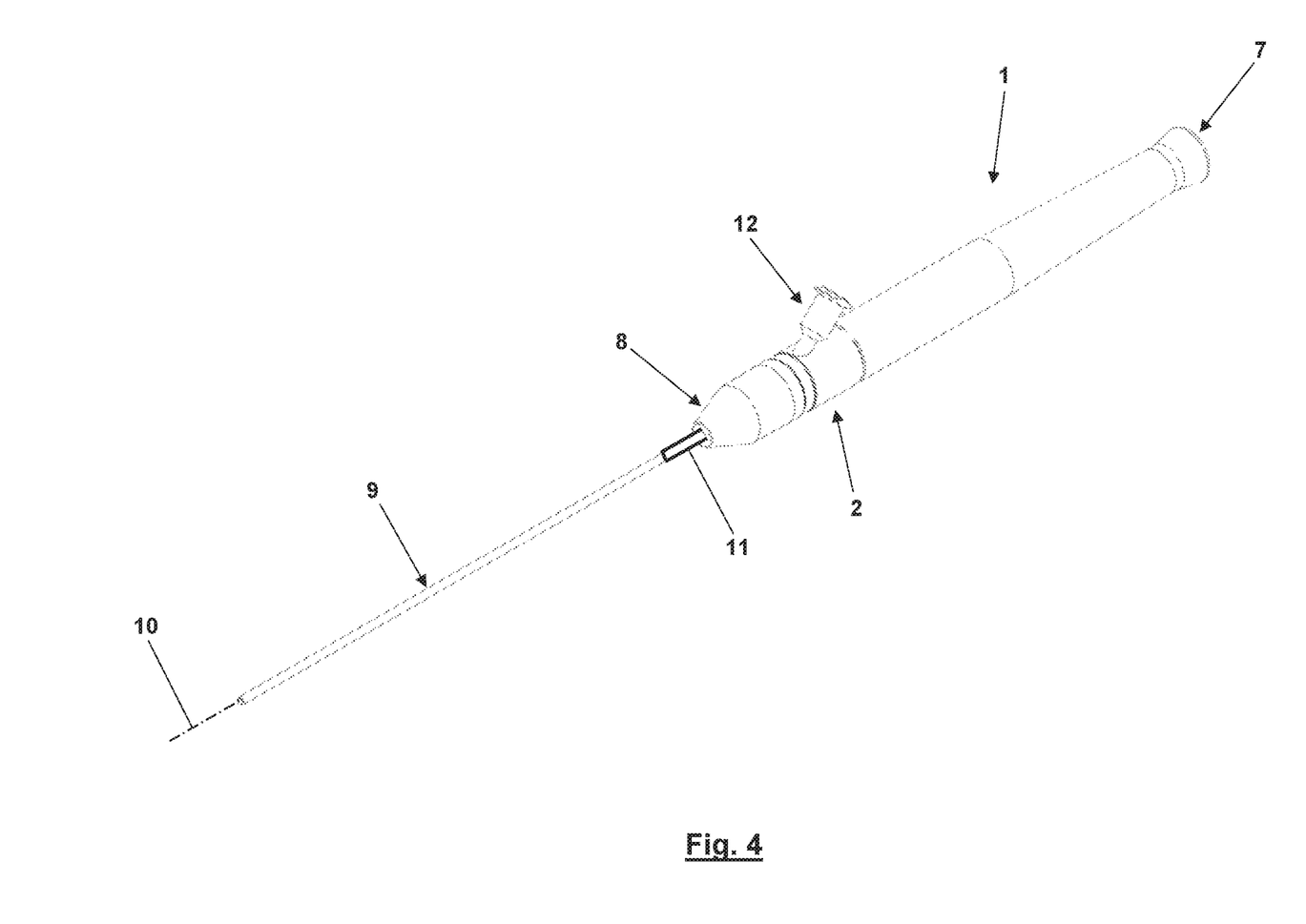
FIG. 4 is a perspective view of the hand piece according to the invention according to FIG. 3 after a hot cleaning of the hand piece at a temperature above a transition temperature of a shape memory alloy, of which the guide tube is made.

FIG. 3 shows the hand piece 1 with the guide tube 9 plastically bent into a freely selected shape. With this shape of the guide tube 9, the hand piece 1 may be used for handling the optical fiber during a laser-surgical intervention. In a hot cleaning and sterilization of the hand piece 1 succeeding to the laser-surgical intervention, the transition temperature of the shaped memory alloy, of which the guide tube 9 is made, is exceeded so that the guide tube 9 returns to its straight base shape as shown in FIG. 4. This straight base shape facilitates a mechanical cleaning of the guide tube 9 and simultaneously indicates that the hand piece 1 has been subjected to an increased temperature in the course of its cleaning and/or sterilization after use.

Many variations and modifications may be made to the preferred embodiments of the invention without departing substantially from the spirit and principles of the invention. All such modifications and variations are intended to be included herein within the scope of the present invention, as defined by the following claims.

I claim:

1. A hand piece for handling an optical fiber during a laser-surgical intervention, the hand piece comprising
    a handle body elongated along a main axis, the handle body having a through hole extending along the main axis,
    a guide tube attached to the handle body, the guide tube having a tube lumen aligned and communicating with the through hole, and
    a fixing device configured for, in direction of the main axis, fixing the optical fiber extending through the through hole and the tube lumen of the guide tube, the fixing device being located in an area of the through hole in the handle body,
    wherein the guide tube is made of a shaped memory alloy which has a transition temperature between 50° C. and 120° C., wherein the guide tube has a straight base shape, wherein the guide tube, below the transition temperature, is bendable by plastic deformation out of the straight base shape into a curved shape, and wherein the guide tube, when heated up above the transition temperature, returns to its straight base shape.

2. The hand piece of claim 1, wherein the guide tube, with its straight base shape, extends along the main axis.

3. The hand piece of claim 1, wherein the transition temperature is between 60 and 90° C.

4. The hand piece of claim 1, wherein a cooling fluid supply connector is attached to the handle body, the cooling fluid supply connector communicating with the tube lumen of the guide tube via the through hole.

5. The hand piece of claim 4, wherein the cooling fluid supply connector is made of PEEK.

6. The hand piece of claim 1, wherein the handle body comprises two handle parts which are screwed together by rotation about the main axis.

7. The hand piece of claim 6, wherein a ring-shaped elastic seal is arranged between the two handle parts which is compressed by screwing the two handle parts together and which, as a part of the fixing device, abuts against the optical fiber.

8. The hand piece of claim 7, wherein a cooling fluid supply connector is attached to the handle body, the cooling fluid supply connector communicating with the tube lumen of the guide tube via the through hole, and wherein the seal is arranged on a side of the cooling fluid supply connector facing away from the guide tube.

9. The hand piece of claim 6, wherein the two handle parts are made of PEEK.

10. The hand piece of claim 6, wherein the two handle parts are made of coated aluminum.

11. The hand piece of claim 10, wherein the aluminum is glass bead blasted.

12. The hand piece of claim 10, wherein the aluminum is DLC coated.

13. The hand piece of claim 1, wherein the guide tube is inserted into a guide tube socket attached to and projecting beyond the handle body.

14. The hand piece of claim 13, wherein the guide tube socket is made of PEEK or high-grade steel.

15. The hand piece of claim 1, wherein an elastic aspirator hose is arranged on the guide tube, an interior diameter of the aspirator hose being larger than an outer diameter of the guide tube.

16. The hand piece of claim 15, wherein an aspirator connector communicating with the aspirator hose is attached to the handle body or to a separate aspirator manifold slid on the guide tube.

17. The hand piece of claim 16, wherein the aspirator connector is made of PEEK or silicone rubber.

18. The hand piece of claim 1, wherein the guide tube is made of nitinol.

19. The hand piece of claim 1,
    wherein a ring-shaped elastic seal is arranged between the two handle parts which is compressed by screwing the two handle parts together and which, as a part of the fixing device, abuts against the optical fiber;
    wherein an elastic aspirator hose is arranged on the guide tube, an interior diameter of the aspirator hose being larger than an outer diameter of the guide tube;
    wherein an aspirator connector communicating with the aspirator hose is attached to the handle body or to a separate aspirator manifold slid on the guide tube; and
    wherein the ring-shaped elastic seal, the elastic aspirator, and the aspirator manifold are made of silicone rubber.

20. An optical fiber handling apparatus comprising
    a first handle part and a second handle part screwed together by rotation about a main axis and together forming a handle elongated along the main axis, the handle having a through hole extending along the main axis through the first handle part and the second handle part,
    a guide tube made of a shaped memory alloy, which has a transition temperature in a range from 60 and 90° C., and attached to the first handle part,
        the guide tube having a tube lumen aligned and communicating with the through hole such as to provide a continuous passage for an optical fiber through the handle and the guide tube,
        the guide tube having a straight base shape extending along the main axis,
        the guide tube, below the transition temperature, being bendable by plastic deformation out of the straight base shape into a curved shape, and
        the guide tube, after a plastic deformation taking place below the transition temperature, returning to the straight base shape upon exceeding the transition temperature,
    a ring-shaped elastic seal arranged between the first handle part and the second handle part, the ring shaped seal being compressed by screwing the first handle part and the second handle part together so that it is pressed against the optical fiber extending through the through hole such as to seal the through hole around the optical fiber and such as to fix the optical fiber with regard to the handle in direction of the main axis, and
    a cooling fluid supply connector arranged at the first handle part and communicating with the through hole up to the elastic seal, and, via the through hole, with the tube lumen of the guide tube.

* * * * *